(12) United States Patent
Blumenfeld et al.

(10) Patent No.: US 9,908,858 B2
(45) Date of Patent: Mar. 6, 2018

(54) METHOD FOR THE SYNTHESIS OF A HYDRAZINE THAT CAN BE USED IN THE TREATMENT OF THE PAPILLOMA VIRUS

(71) Applicant: AVIRAGEN THERAPEUTICS, INC., Alpharetta, GA (US)

(72) Inventors: Marta Blumenfeld, Paris (FR); Delphine Compere, Sceaux (FR); Marco A. Ciufolini, Vancouver (CA)

(73) Assignee: AVIRAGEN THERAPEUTICS, INC., Alpharetta, GA (US)

( * ) Notice: Subject to any disclaimer, the term of this patent is extended or adjusted under 35 U.S.C. 154(b) by 0 days.

(21) Appl. No.: 14/655,266

(22) PCT Filed: Dec. 27, 2013

(86) PCT No.: PCT/EP2013/078035
§ 371 (c)(1),
(2) Date: Jun. 24, 2015

(87) PCT Pub. No.: WO2014/102313
PCT Pub. Date: Jul. 3, 2014

(65) Prior Publication Data
US 2015/0353517 A1 Dec. 10, 2015

(30) Foreign Application Priority Data

Dec. 27, 2012 (FR) ...................... 12 62872

(51) Int. Cl.
C07D 211/26 (2006.01)
C07D 211/28 (2006.01)
C07D 295/135 (2006.01)
C07D 295/155 (2006.01)

(52) U.S. Cl.
CPC ..... C07D 295/135 (2013.01); C07D 295/155 (2013.01)

(58) Field of Classification Search
None
See application file for complete search history.

(56) References Cited

U.S. PATENT DOCUMENTS 9,452,991 B2 9/2016 Blumenfeld et al.
2009/0209586 A1 8/2009 Blumenfeld

OTHER PUBLICATIONS

Collet, A. et al. Practical Synthesis of Optically Active α-Hydrazino Acids from α-Amino Acids. Tetrahedron. 1987, vol. 43, p. 891.*
Viret et al., "Practical synthesis of optically active á-hydrazino acids from á-amino acids," Tetrahedron, vol. 43, No. 5, pp. 891-894, 1987.
International Search Report issued in application No. PCT/EP2013/078035 dated May 3, 2014.
Translation of Official Action from Japanese Patent Office, dated Nov. 28, 2016.
Viret, Joelle, et al., Practical Synthesis of Optically Active α-Hydrazino Acids from α-Amino Acids, Tetrahedron, 1987, vol. 43, No. 5, p. 891-894.
Murakami, Yasuoki, et al., "An Efficient Synthesis of 1, 1-Disubstituted Hydrazines", Chem. Pharm. Bull., 1983, vol. 31, No. 2, p. 423-428.
Murakami, et al., An Efficient Method for Synthesis of 1, 1-Diarylhydrazines as an Intermediate for Indole Synthesis, Heterocycles, 1979, vol. 12, No. 12, p. 1571-1574.

* cited by examiner

*Primary Examiner* — Andrew D Kosar
*Assistant Examiner* — Ben S Michelson
(74) *Attorney, Agent, or Firm* — B. Aaron Schulman, Esq.; Stites & Harbison, PLLC

(57) ABSTRACT

The invention relates to a method for producing a hydrazine of general formula (I) and the pharmaceutically acceptable salts thereof from an amine of formula (II), characterised in that said method uses a urea of formula (III) as a synthesis intermediate.

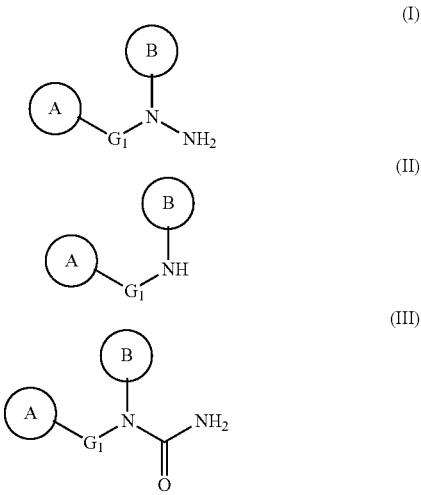

15 Claims, No Drawings

METHOD FOR THE SYNTHESIS OF A HYDRAZINE THAT CAN BE USED IN THE TREATMENT OF THE PAPILLOMA VIRUS

The present invention relates to a novel method for the synthesis of compounds that can be used in the treatment of the papilloma virus described particularly in application WO 2007/135106.

The compounds described in application WO 2007/135106 have the following structure:

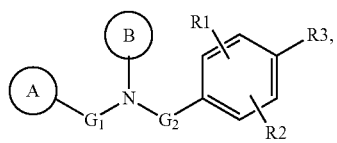

wherein:
- A is an optionally substituted aryl, cycloalkyl, cycloalkenyl or heterocycle group,
- B is an optionally substituted aryl or heterocycle,
- R1 and R2 are independently a hydrogen atom or various substituents,
- R3 is an acid functional group or a prodrug radical or a bioisostere of this functional group,
- $G_1$ is a bond or a hydrocarbon chain, and
- $G_2$ is a

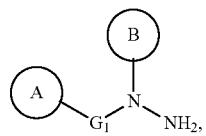

group, where R is a hydrogen atom or various substituents, W is O, S or NH and G is a bond or a hydrocarbon chain.

The method for the synthesis of these compounds described in application WO 2007/135106 uses as a synthesis intermediate a hydrazine of the following structure:

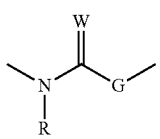

(I)

which is itself prepared from the amine of the following structure:

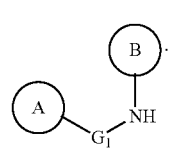

(II)

Production of hydrazine from the corresponding amine is carried out by nitrosation of the amine in the presence of $NaNO_2$ to give the corresponding N-nitroso compound, which is then reduced to give hydrazine. However, since nitroso compounds are dangerous to use, such a synthesis pathway is not suitable from an industrial point of view. Moreover, rather strict standards concerning acceptable residual concentrations of nitroso compounds in pharmaceutical products lead to the consideration of another synthesis pathway.

The Inventors thus discovered that it was possible to produce the desired hydrazine from the corresponding amine by using a urea intermediate and not an N-nitroso compound.

The subject matter of the present invention is thus a method for producing a hydrazine of general formula (I):

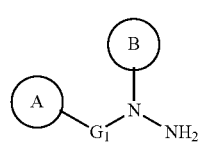

(I)

and the pharmaceutically acceptable salts thereof, wherein:
- $G_1$ is a bond or a linear or branched, saturated or unsaturated hydrocarbon chain comprising 1 to 4 carbon atoms, optionally substituted by one or two preferably identical alkyl groups,
- A is an aryl group, such as phenyl, optionally substituted:
  - in the meta or para position by:
    - a halogen atom or a cyano, alkoxy, haloalkoxy, acylaminoalkyl or —XR group where X is —O—, —S—, —SO—, —SO₂— or —CO— and R is an arylalkyl, cycloalkyl or aryl group, each optionally substituted by one or two identical or different substituents, such as a halogen atom, an alkoxy or acyl group, or
    - a cycloalkyl, aryl or arylalkyl group, each optionally substituted by one or two identical or different substituents, such as an acyl or alkoxy group,
  - and/or in the ortho or meta position by an alkyl group, and
- B is an aryl group, preferably a phenyl, substituted in the ortho position by a heterocycle, preferably an N-cycloalkyl, such as a piperidin-1-yl group, and optionally substituted in the ortho' position by an alkyl group, such as a methyl, from an amine of formula (II):

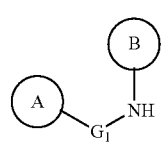

(II)

wherein $G_1$, A and B are as defined above,
characterized in that said method uses a urea of formula (III) as a synthesis intermediate:

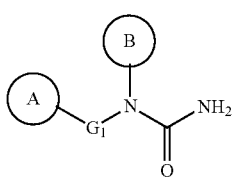

(III)

wherein G₁, A and B are as defined above.

In the present invention, by "pharmaceutically acceptable" is meant that which can be used in the production of a pharmaceutical composition and which is generally safe, nontoxic and neither biologically nor otherwise undesirable and which is acceptable for veterinary use as well as human pharmaceutical use.

By "pharmaceutically acceptable salts" of a compound is meant to indicate in the present invention salts that are pharmaceutically acceptable, as defined herein, and that have the desired pharmacological activity of the parent compound. Such salts comprise:
(1) hydrates and solvates,
(2) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalene-sulfonic acid, propionic acid, salicylic acid, succinic acid, dibenzoyl-L-tartaric acid, tartaric acid, p-toluenesulfonic acid, trimethylacetic acid, trifluoroacetic acid and the like; and
(3) salts formed when an acidic proton present in the parent compound either is replaced by a metal ion, for example an alkaline metal ion (Na⁺, K⁺ or Li⁺, for example), an alkaline-earth metal ion (such as Ca²⁺ or Mg²⁺) or an aluminum ion; or coordinates with an organic or inorganic base. Acceptable organic bases comprise diethanolamine, ethanolamine, N-methylglucamine, triethanolamine, tromethamine and the like. Acceptable inorganic bases comprise aluminum hydroxide, calcium hydroxide, potassium hydroxide, sodium carbonate and sodium hydroxide.

By "unsaturated" is meant, in the context of the present invention, that the group comprises one or more unsaturations.

By "unsaturation" is meant, in the context of the present invention, a double bond or a triple bond.

By "halogen" is meant, in the context of the present invention, a fluorine, bromine, chlorine or iodine atom. Advantageously, it is a fluorine, bromine or chlorine atom.

By "alkyl" group is meant, in the context of the present invention, a linear or branched saturated hydrocarbon chain comprising 1 to 6 carbon atoms, in particular methyl, ethyl, n-propyl, isopropyl, n-butyl, isobutyl, sec-butyl, tert-butyl, n-pentyl or n-hexyl groups. Advantageously, it is methyl.

By "cycloalkyl" group is meant, in the context of the present invention, a saturated monocyclic or polycyclic system, preferably a saturated mono-, bi- or tricyclic system, comprising 3 to 12 carbon atoms, wherein the ring pairs may be fused or bridged, such as cyclopropyl, cyclopentyl, cyclohexyl, cycloheptyl, cyclooctyl, adamantyl, decalinyl or norbornyl groups.

By "N-cycloalkyl" group is meant, in the context of the present invention, a cycloalkyl group as defined above wherein a carbon atom has been substituted by a nitrogen atom, the link with the molecule being made by means of this nitrogen atom. It is advantageously a piperidin-1-yl or pyrrolidin-1-yl group.

By "acyl" group is meant, in the context of the present invention, a group of formula —C(O)—Z, where Z is an alkyl group as defined above or a phenyl. It may be advantageously an acetyl, ethylcarbonyl or benzoyl group.

By "alkoxy" group is meant, in the context of the present invention, an alkyl group as defined above linked to the molecule by means of an oxygen atom. It may be in particular a methoxy, ethoxy, n-propoxy, isopropoxy, n-butoxy, iso-butoxy, sec-butoxy or tert-butoxy group.

By "haloalkoxy" group is meant, in the context of the present invention, an alkoxy group as defined above substituted by one or more halogen atom(s) as defined above. Preferably, it will be fluoroalkoxy, that is, an alkoxy group substituted by one or more fluorine atom(s), such as an —OCF₃ or —OCH₂CF₃ group.

By "aryl" group is meant, in the context of the present invention, an aromatic group preferably comprising 5 to 10 carbon atoms and comprising one or more joined rings, such as, for example, a phenyl or naphthyl group. Advantageously, it is phenyl.

By "heterocycle" is meant, in the context of the present invention, a saturated, unsaturated or aromatic monocyclic or polycyclic system, and preferably a saturated, unsaturated or aromatic mono- or bi-cyclic system, comprising 3 to 12 members, wherein the ring pairs may be fused, spiro-fused or bridged, and comprising 1 to 4 identical or different heteroatoms selected from O, S and N, and optionally comprising one or two oxo or thioxo groups, with the understanding that in the case of a polycyclic system one of the rings may be aromatic whereas the other(s) may be aromatic, saturated or unsaturated. Advantageously, it will be piperidyl, piperazyl, furyl, thienyl, pyrrolyl, pyrazolyl, imidazolyl, pyridyl, pyrimidyl, pyrazinyl, pyradizinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, [1,2,3]triazolyl and [1,2,4]triazolyl groups.

By "arylalkyl" group is meant, in the context of the present invention, an aryl group as defined above linked to the molecule by means of an alkyl group as defined above. Preferably, it is a benzyl group.

By "acylaminoalkyl" is meant, in the context of the present invention, a group of formula -Alk-NHCO-Alk', where Alk and Alk' independently represent an alkyl group as defined above.

The hydrazine of formula (I) as defined above may thus be produced from the urea of formula (III) as defined above by Shestakov rearrangement.

This reaction is described in the literature for variously substituted ureas (Viret J. et al. *Tetrahedron* 1987, 43, 891-894; Murakami Y. et al. *Chem. Pharm. Bull.* 1983, 31, 423-428; Murakami Y. and Yokotama Y. *Heterocycles* 1979, 12, 1571-1574).

This Shestakov rearrangement will be advantageously carried out in the presence of a rearrangement inducing agent selected from NaOCl and KOCl, and preferably being NaOCl.

Preferably, the rearrangement inducing agent is introduced in a staggered fashion. Thus, the inducing agent may be introduced in several portions spread over time, or dropwise, or in a continuous and slow manner such that the addition is sufficiently spread over time. The person skilled in the art will be able to adapt the addition parameter (such as addition rate for continuous addition) of the inducing agent such that the addition is optimal.

At least 1 molar equivalent, advantageously between 1 and 1.5 molar equivalents, and preferably about 1 molar equivalent, of rearrangement inducing agent is used in this reaction, for 1 molar equivalent of the urea of formula (III).

Surprisingly, the Inventors noticed that better yields were obtained when the rearrangement inducing agent was added to the reaction medium gradually, compared to a single addition.

Obviously, the number of portions added and the duration of the addition will depend on the scale at which the reaction is carried out, such adaptations being the common practice of the person skilled in the art.

Shestakov rearrangement may be carried out in a dioxane/water mixture or in alcohol as solvent, and preferably in tert-butanol.

By "alcohol" is meant, in the context of the present invention, a compound of formula Alk-OH, where Alk is an alkyl group as defined above. Preferably, it is methanol, ethanol or tert-butanol.

This rearrangement is carried out advantageously under basic conditions, particularly in the presence of sodium hydroxide or potassium hydroxide, and preferably in the presence of potassium hydroxide.

Furthermore, the urea of formula (III) as defined above may be produced from the amine of formula (II) as defined above according to the following steps:
(1) reaction of the amine of formula (II) with trichloroacetyl isocyanate ($Cl_3CC(O)-N=C=O$) to give the compound of formula (IV):

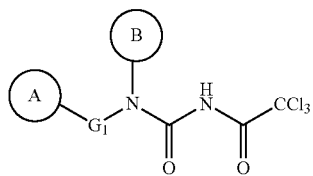

(IV)

wherein $G_1$, A and B are as defined above, and
(2) treatment in basic medium of the compound of formula (IV) obtained in the preceding step to give a urea of formula (III).

Step (1) may be carried out in a solvent such as acetonitrile, tetrahydrofuran, dichloromethane or dioxane, and preferably in acetonitrile.

Step (1) may be carried out at room temperature, that is, at temperatures varying between 20 and 40° C., and preferably at about 25° C.

Sodium or potassium hydroxide, and preferably KOH, may be used as a base in step (2).

The solvent used in this step (2) will be an alcohol as defined above and preferably will be methanol, step (2) being carried out in particular at reflux of this solvent.

Thus, according to a particular embodiment of the method of the invention, the hydrazine of preceding formula (I) may be produced according to the following successive steps:
(1) reaction of an amine of formula (II) as defined above with $Cl_3CC(O)-N=C=O$ to give a compound of formula (IV) as defined above,
(2) treatment in basic medium of the compound of formula (IV) obtained in the preceding step to give a urea of formula (III) as defined above,
(3) Shestakov reaction starting from the urea of formula (III) obtained in the preceding step to give a hydrazine of formula (I) as defined above, and
(4) isolation from the reaction medium of the hydrazine of formula (I) obtained in the preceding step.

Isolation of the final product may be carried out by techniques well-known to the person skilled in the art, such as, for example, by extraction, solvent evaporation or by precipitation and filtration.

The hydrazine thus obtained may in addition be purified if necessary by methods well-known to the person skilled in the art, such as by recrystallization if the compound is crystalline, or by distillation.

Advantageously, $G_1$ is a bond or a linear and saturated hydrocarbon chain comprising 1 to 4 carbon atoms, and preferably is a bond.

Advantageously, radical A defined above is an aryl, preferably a phenyl, substituted in the meta or para position, preferably in the para position, by an alkoxy group, such as methoxy, or by an aryl or arylalkyl group, such as phenyl or benzyl, optionally substituted by one or two identical or different substituents, such as an acyl or alkoxy group.

Advantageously, B is an aryl group, preferably a phenyl, substituted in the ortho position by a heterocycle, preferably an N-cycloalkyl, such as a piperidin-1-yl group, and optionally substituted in the ortho' position by an alkyl group, such as a methyl.

In particular, the hydrazine of formula (I) is N-(4-benzyl-phenyl)-N-(2-methyl-6-piperidin-1-yl-phenyl)-hydrazine (hydrazine (Ia)).

Consequently, preceding hydrazine (Ia) is produced from 1-(4-benzyl-phenyl)-1-(2-methyl-6-piperidin-1-yl-phenyl)-urea (compound (IIIa)), itself produced from (4-benzyl-phenyl)-(2-methyl-6-piperidin-1-yl-phenyl)-amine (compound (IIa)).

Another subject matter of the present invention is a method for producing a compound of formula (V) as follows:

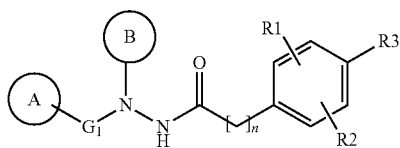

(V)

and the pharmaceutically acceptable salts thereof,
wherein:
R1 is an alkoxy group, such as methoxy, preferably in the ortho position relative to R3,
R2 is a hydrogen or halogen atom, such as chlorine or bromine, or an alkyl group, such as methyl, preferably in the meta position relative to R3,
R3 is an acid or ester group, and preferably an acid group,
n is an integer between 1 and 4, preferably between 1 and 2, and more preferably is 1,
$G_1$ is a bond or a linear or branched, saturated or unsaturated hydrocarbon chain comprising 1 to 4 carbon atoms, optionally substituted by one or two preferably identical alkyl groups,
A is an aryl group, such as phenyl, optionally substituted:
in the meta or para position by:
a halogen atom or a cyano, alkoxy, haloalkoxy, acylaminoalkyl or —XR group where X is —O—, —S—, —SO—, —SO$_2$— or —CO— and R is an arylalkyl, cycloalkyl or aryl group, each optionally substituted by one or two identical or different substituents, such as a halogen atom, an alkoxy or acyl group, or a cycloalkyl, aryl or arylalkyl group, each optionally substituted by one or two identical or different substituents, such as an acyl or alkoxy group, and/or in the ortho or meta position by an alkyl group, and B is an aryl group, preferably a phenyl, substituted in the ortho position by a heterocycle, preferably an N-cycloalkyl, such as a piperidin-1-yl group, and optionally substituted in the ortho' position by an alkyl group, such as a methyl, characterized in that it comprises a method for producing a compound of formula (I) as defined above.

The compounds of formula (V) correspond to compounds that can be used in the treatment of the papilloma virus described in application WO 2007/135106. This patent application further describes the method for producing compounds of formula (V) from the hydrazine of formula (I), as well as the method for producing the amines of formula (II).

By "acid" is meant, in the context of the present invention, a COOH group.

By "ester" is meant, in the context of the present invention, a —CO—O-Alk group, where Alk is an alkyl group as defined above.

Advantageously, R2 is a halogen atom, such as a bromine atom, preferably in the meta position relative to R3.

Advantageously, $G_1$ is a bond or a linear and saturated hydrocarbon chain comprising 1 to 4 carbon atoms, and preferably is a bond.

Advantageously, radical A defined above is an aryl, preferably a phenyl, substituted in the meta or para position, preferably in the para position, by an alkoxy group, such as methoxy, or by an aryl or arylalkyl group, such as phenyl or benzyl, optionally substituted by one or two identical or different substituents, such as an acyl or alkoxy group.

Advantageously, B is an aryl group, preferably a phenyl, substituted in the ortho position by a heterocycle, preferably an N-cycloalkyl, such as a piperidin-1-yl group, and optionally substituted in the ortho' position by an alkyl group, such as a methyl.

Preferably, the compound of formula (V) has the following features:

A is a phenyl group substituted in the para position by a benzyl group,

B is a phenyl group substituted in the ortho position by a piperidin-1-yl group and in the ortho' position by a methyl group, $G_1$ is a bond, and R1, R2, R3 and n are as defined above.

In particular, the compound of formula (V) is 4-[N'-(4-benzyl-phenyl)-N'-(2-methyl-6-piperidin-1-yl-phenyl)-hydrazinocarbonyl methyl]-5-bromo-2-methoxy-benzoic acid hydrochloride (compound (Va)).

Consequently, compound (Va) may be produced from intermediates (Ia), (IIa) and (IIIa) mentioned above.

Another subject matter of the present invention is a compound of general formula (III):

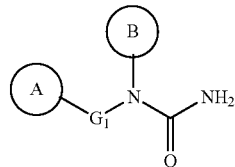

(III)

wherein:

$G_1$ is a bond or a linear or branched, saturated or unsaturated hydrocarbon chain comprising 1 to 4 carbon atoms, optionally substituted by one or two preferably identical alkyl groups, A is an aryl group, such as phenyl, optionally substituted:

in the meta or para position by:

a halogen atom or a cyano, alkoxy, haloalkoxy, acylaminoalkyl or —XR group where X is —O—, —S—, —SO—, —SO$_2$— or —CO— and R is an arylalkyl, cycloalkyl or aryl group, each optionally substituted by one or two identical or different substituents, such as a halogen atom, an alkoxy or acyl group, or a cycloalkyl, aryl or arylalkyl group, each optionally substituted by one or two identical or different substituents, such as an acyl or alkoxy group, and/or in the ortho or meta position by an alkyl group, and B is an aryl group, preferably a phenyl, substituted in the ortho position by a heterocycle, preferably an N-cycloalkyl, such as a piperidin-1-yl group, and optionally substituted in the ortho' position by an alkyl group, such as a methyl.

Advantageously, $G_1$ is a bond or a linear and saturated hydrocarbon chain comprising 1 to 4 carbon atoms, and preferably is a bond.

Advantageously, the radical A defined above is an aryl, preferably a phenyl, substituted in the meta or para position, preferably in the para position, by an alkoxy group, such as methoxy, or by an aryl or arylalkyl group, such as phenyl or benzyl, optionally substituted by one or two identical or different substituents, such as an acyl or alkoxy group.

Advantageously, B is an aryl group, preferably a phenyl, substituted in the ortho position by a heterocycle, preferably an N-cycloalkyl, such as a piperidin-1-yl group, and optionally substituted in the ortho' position by an alkyl group, such as a methyl.

In particular, compound (III) will be 1-(4-benzyl-phenyl)-1-(2-methyl-6-piperidin-1-yl-phenyl)-urea (compound (IIIa)).

The present invention will be better understood in the light of the following non-limiting examples.

EXAMPLE

Abbreviations used in the procedures:

TLC Thin-layer chromatography eq Molar equivalent

HPLC High-performance liquid chromatography

NMR Nuclear magnetic resonance

MS Mass spectrometry

Example: Synthesis of Compound (Va)

Stage 1: Synthesis of Amine (IIa)

This compound is synthesized according to the procedure described in application WO 2007/135106. It corresponds to the compound obtained in stage 3 of example 27 of this application (pages 90-91).

Stage 2: Synthesis of Urea (IIIa)

Step (1)

To a suspension of amine (Ia) (4.00 g, 11.23 mmol, 1.0 eq) in anhydrous acetonitrile (100 ml), under argon and under stirring, trichloroacetyl isocyanate (2.53 g, 13.48 mmol, 1.2 eq) is added dropwise at 18° C. for 10 minutes. The resulting clear yellow solution is stirred for an additional 15 minutes at room temperature. After complete consumption of amine (IIa) (monitored by TLC and HPLC), the solvent is evaporated under reduced pressure. The clear brown crude intermediate compound thus obtained (6.2 g, quantitative yield) is used directly in the following step without additional purification.

Yield: quantitative

HPLC: 92.24%

$^1$H NMR (CDCl$_3$, 200 MHz) δ (ppm): 8.80 (broad s, 1H), 6.95-7.31 (m, 12H), 3.92 (s, 2H), 2.86 (m, 2H), 2.73 (m, 2H), 2.03 (s, 3H), 1.53 (m, 6H)

Step (2)

To a solution of the crude intermediate obtained in step (1) above (6.13 g, 11.2 mmol, 1.0 eq) in methanol (120 ml), KOH aqueous solution (12.73 g of KOH, 224.0 mmol, 20 eq, in 25 ml of water) is added under stirring. The reaction mixture is then heated at 75° C. with shaking for 1.5 hours at the same temperature. After complete consumption of the intermediate (monitored by TLC), the reaction mixture is concentrated to dryness.

The resulting crude mixture is then taken up in water (100 ml) and extracted with ethyl acetate (3×100 ml). The combined organic phases are dried on sodium sulfate, filtered and concentrated under reduced pressure to give the desired urea (IIIa) (4.43 g, 11.1 mmol, 99% yield) in the form of a colorless gum with a purity of 83% determined by HPLC. This urea is then used as such in the following step.

Yield: 99%

MS: MH$^+$400

HPLC: 83.01%

$^1$H NMR (CDCl$_3$, 200 MHz) δ (ppm): 6.94-7.30 (m, 12H), 4.77 (s, 2H), 3.91 (s, 2H), 2.91 (m, 2H), 2.60 (m, 2H), 2.26 (s, 3H), 1.48 (m, 6H).

Stage 3: Synthesis of Hydrazine (Ia)

To a solution of crude urea (IIIa) obtained in preceding stage 2 (4.43 g, 11.1 mmol, 1 eq) in tert-butanol (50 ml), KOH aqueous solution (12.58 g of KOH, 222.1 mmol, 20 eq, in 25 ml of water) is added at 18° C. under stirring for 10 minutes. To the resulting reaction mixture, NaOCl aqueous solution (8.21 ml, 11.1 mmol, 10% active chlorine) is added in portions (1 ml every 15 minutes) over a period of 2.25 hours. After vigorous stirring at 18° C. for an additional 15 minutes, the phases are separated. The reaction mixture is extracted with ethyl acetate (3×100 ml). The combined organic phases are concentrated to dryness under reduced pressure to give the desired hydrazine (4 g, 83% purity determined by HPLC). The residue thus obtained is then purified by flash chromatography on a silica gel column (eluent: 95/5 cyclohexane/ethyl acetate) to give the desired hydrazine (3.4 g, 9.1 mmol, 81% total yield) in the form of a cream-colored solid with a purity of 95.6% determined by HPLC.

Total yield: 81%

MS: MH$^+$ 372

HPLC: 95.60%

$^1$H NMR (CDCl$_3$, 400 MHz) δ (ppm): 7.25 (m, 2H), 7.14 (m, 4H), 6.97 (m, 4H), 6.73 (m, 2H), 4.83 (broad s, 2H), 3.87 (s, 2H), 2.80 (broad s, 4H), 2.08 (s, 3H), 1.46-1.57 (m, 6H).

Stage 4: Synthesis of Compound (Va)

This compound is produced from hydrazine (Ia) obtained in preceding stage 3 according to the protocol described in application WO 2007/135106. This protocol is described in example 27 of this application, and corresponds to stages 5 and 6 of this example (pages 91-92).

The invention claimed is:

1. A method for producing a compound of formula (I):

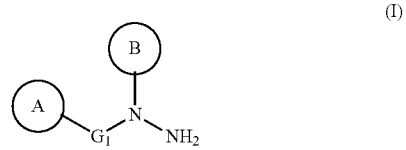

and the pharmaceutically acceptable salts thereof, wherein:

G$_1$ is a bond or a linear or branched, saturated or unsaturated hydrocarbon chain comprising 1 to 4 carbon atoms, optionally substituted by one or two alkyl groups, A is an aryl group optionally substituted:

in the meta or para position by:

a halogen atom or a cyano, alkoxy, haloalkoxy, acylaminoalkyl or —XR group where X is —O—, —S—, —SO—, —SO$_2$— or —CO— and R is an arylalkyl, cycloalkyl or aryl group, each optionally substituted by one or two identical or different substituents selected from the group consisting of a halogen atom, an alkoxy, and an acyl group, or a cycloalkyl, aryl or arylalkyl group, each optionally substituted by one or two identical or different substituents selected from the group consisting of an alkoxy and an acyl group, and/or in the ortho or meta position by an alkyl group, and B is an aryl group substituted in the ortho position by a heterocycle and optionally substituted in the ortho' position by an alkyl group, comprising reacting an amine of formula (II):

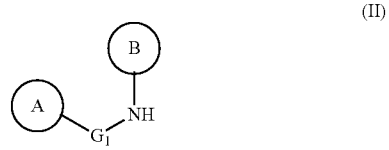

wherein $G_1$, A and B are as defined above,
to produce a urea of formula (III) as a synthesis intermediate:

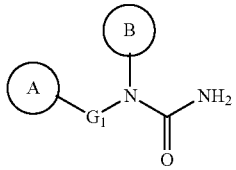

(III)

wherein $G_1$, A and B are as defined above,
wherein the urea of formula (III) is produced from the amine of formula (II) according to the following steps:
(1) reacting the amine of formula (II) with $Cl_3CC(O)$—N=C=O to give the compound of formula (IV) as follows:

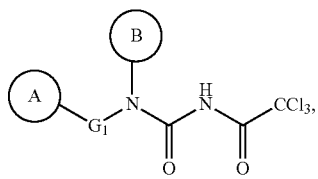

(IV)

wherein $G_1$, A and B are as defined above, and
(2) treating in basic medium the compound of formula (IV) obtained in the preceding step to give a urea of formula (III),
and reacting formula (III) to obtain formula (I).

2. The method according to claim 1, wherein the compound of formula (I) is produced from the urea of formula (III) by means of Shestakov rearrangement.

3. The method according to claim 2, wherein the Shestakov rearrangement is carried out in the presence of a rearrangement inducing agent selected from the group consisting of NaOCl and KOCl.

4. The method according to claim 3, wherein the rearrangement inducing agent is introduced in a staggered fashion.

5. The method according to claim 1, wherein A is an aryl substituted in the meta or para position by an alkoxy group or by an aryl or arylalkyl group optionally substituted by one or two identical or different substituents selected from an acyl group and an alkoxy group.

6. The method according to claim 1, wherein B is an aryl group substituted in the ortho position by an N-cycloalkyl and optionally substituted in the ortho' position by an alkyl group.

7. The method according to claim 1, wherein A is a phenyl substituted in the para position by an alkoxy group or by an aryl or arylalkyl group optionally substituted by one or two identical or different substituents selected from an acyl group and an alkoxy group and B is a phenyl substituted in the ortho position by a piperidin-1-yl group and optionally substituted in the ortho' position by a methyl.

8. The method according to claim 1, wherein the compound of formula (I) is N-(4-benzyl-phenyl)-N-(2-methyl-6-piperidin-1-yl-phenyl)-hydrazine.

9. A method for producing a compound of following formula (V):

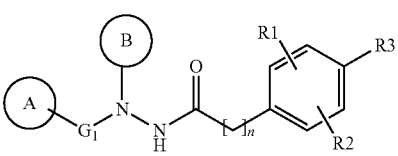

(V)

and the pharmaceutically acceptable salts thereof,
wherein:
R1 is an alkoxy group,
R2 is a hydrogen or halogen atom or an alkyl group,
R3 is an acid or ester group,
n is an integer between 1 and 4,
$G_1$ is a bond or a linear or branched, saturated or unsaturated hydrocarbon chain comprising 1 to 4 carbon atoms, optionally substituted by one or two alkyl groups,
A is an aryl group optionally substituted:
in the meta or para position by:
a halogen atom or a cyano, alkoxy, haloalkoxy, acylaminoalkyl or —XR group where X is —O—, —S—, —SO—, —$SO_2$— or —CO— and R is an arylalkyl, cycloalkyl or aryl group, each optionally substituted by one or two identical or different substituents selected from the group consisting of a halogen atom, an alkoxy, and an acyl group, or
a cycloalkyl, aryl or arylalkyl group, each optionally substituted by one or two identical or different substituents selected from the group consisting of an alkoxy and an acyl group,
and/or in the ortho or meta position by an alkyl group, and
B is an aryl group substituted in the ortho position by a heterocycle and optionally substituted in the ortho' position by an alkyl group,
comprising reacting a compound of formula (I) obtained by the method according to claim 1.

10. The method according to claim 9, wherein in the compound of formula (V) produced by said method, R1 is a methoxy, R2 is a hydrogen, a chlorine, a bromine, or a methyl, and R3 is an acid group.

11. The method according to claim 9, wherein in the compound of formula (V) produced by said method, R1 is in the ortho position relative to R3 and R2 is in the meta position relative to R3.

12. The method according to claim 9, wherein in the compound of formula (V) produced by said method, n is 1 or 2.

13. The method according to claim 9, wherein in the compound of formula (V) produced by said method, B is an aryl group substituted in the ortho position by an N-cycloalkyl and optionally substituted in the ortho' position by an alkyl group.

14. The method according to claim 9, wherein in the compound of formula (V) produced by said method, A is a phenyl substituted in the para position by an alkoxy group or by an aryl or arylalkyl group optionally substituted by one or two identical or different substituents selected from an acyl group and an alkoxy group and B is a phenyl substituted in the ortho position by a piperidin-1-yl group and optionally substituted in the ortho' position by a methyl.

15. The method according to claim 9, wherein the compound of formula (V) produced by said method is 4-[N'-(4-benzyl-phenyl)-N'-(2-methyl-6-piperidin-1-yl-phenyl)hydrazinocarbonyl methyl]-5-bromo-2-methoxy-benzoic acid hydrochloride.

* * * * *